(12) United States Patent
Besch et al.

(10) Patent No.: US 8,746,251 B2
(45) Date of Patent: Jun. 10, 2014

(54) PROTECTIVE STORAGE FOR A NASAL CANNULA ASSEMBLY

(76) Inventors: Kurt Besch, New Port Richey, FL (US); Richard R. Gilbert, II, Clearwater, FL (US)

( * ) Notice: Subject to any disclaimer, the term of this patent is extended or adjusted under 35 U.S.C. 154(b) by 1007 days.

(21) Appl. No.: 12/776,537

(22) Filed: May 10, 2010

(65) Prior Publication Data
US 2011/0272313 A1 Nov. 10, 2011

(51) Int. Cl.
*A61M 15/08* (2006.01)
*B65D 83/10* (2006.01)

(52) U.S. Cl.
USPC ........................... 128/207.18; 206/363

(58) Field of Classification Search
USPC ........ 206/363, 364, 438; 128/203.18, 206.11, 128/207.14–207.18
See application file for complete search history.

(56) References Cited

U.S. PATENT DOCUMENTS

| | | |
|---|---|---|
| 4,106,505 A | 8/1978 | Salter et al. |
| 4,273,124 A | 6/1981 | Zimmerman |
| 4,367,735 A | 1/1983 | Dali |
| 4,422,456 A | 12/1983 | Tiep |
| 4,648,398 A | 3/1987 | Agdanowski et al. |
| 4,753,233 A | 6/1988 | Grimes |
| 4,808,160 A | 2/1989 | Timmons et al. |
| 5,025,805 A | 6/1991 | Nutter |
| 5,437,267 A * | 8/1995 | Weinstein et al. ....... 128/207.18 |
| 5,509,409 A | 4/1996 | Weatherholt |
| 6,439,234 B1 | 8/2002 | Curti et al. |
| 6,655,385 B1 | 12/2003 | Curti et al. |
| 6,679,265 B2 | 1/2004 | Strickland et al. |
| 7,007,694 B2 | 3/2006 | Aylsworth et al. |
| 7,047,974 B2 | 5/2006 | Strickland et al. |
| D533,269 S | 12/2006 | McAuley et al. |
| 7,146,976 B2 | 12/2006 | McKown |
| 7,156,097 B2 | 1/2007 | Cardoso |
| 7,353,826 B2 | 4/2008 | Sleeper et al. |
| 7,614,401 B2 | 11/2009 | Thompson |
| D612,148 S * | 3/2010 | Treece et al. ............... D3/203.1 |
| 7,798,332 B1 * | 9/2010 | Brunet .......................... 206/364 |
| 2009/0101142 A1 | 4/2009 | Lang |
| 2009/0199858 A1 * | 8/2009 | Hagberg et al. .......... 128/207.18 |
| 2009/0292258 A1 * | 11/2009 | Turner ......................... 604/263 |
| 2010/0059053 A1 * | 3/2010 | Niland ..................... 128/203.18 |

* cited by examiner

*Primary Examiner* — Bryon Gehman
(74) *Attorney, Agent, or Firm* — Erickson Kernell Derusseau & Kleypas, LLC

(57) ABSTRACT

A protective storage capsule is disclosed for a nasal cannula. The protective storage capsule may be used in conjunction with a nasal cannula assembly. The protective storage capsule includes a housing adapted to receive the nasal cannula and a cap to cover and protect the nasal cannula from dirt and debris when not being worn by a patient. The protective storage capsule slides along one or more of the support tubes of the nasal cannula assembly. The surfaces of the protective storage capsule may be treated with an antimicrobial film or be infused with antimicrobial nanoparticles.

40 Claims, 7 Drawing Sheets

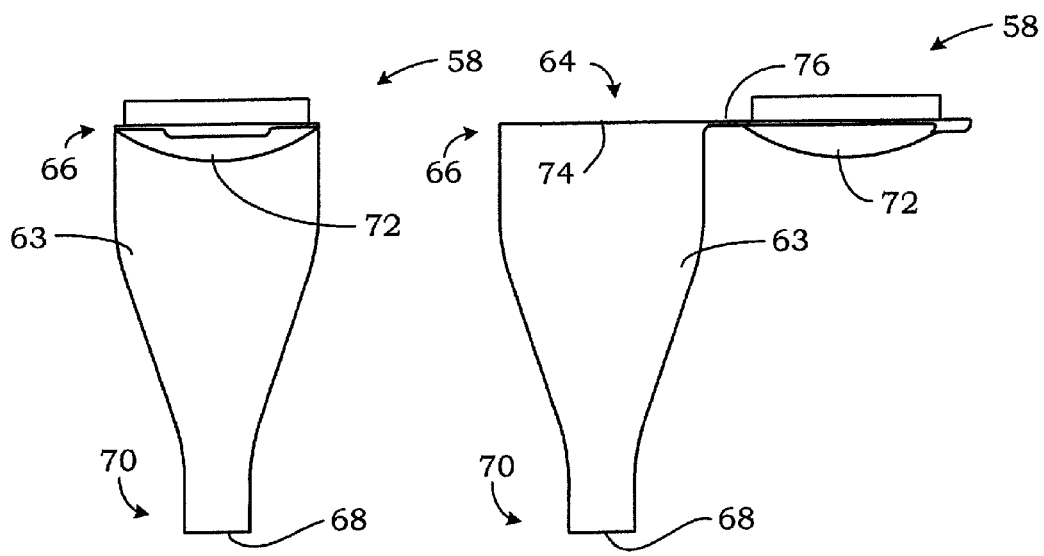
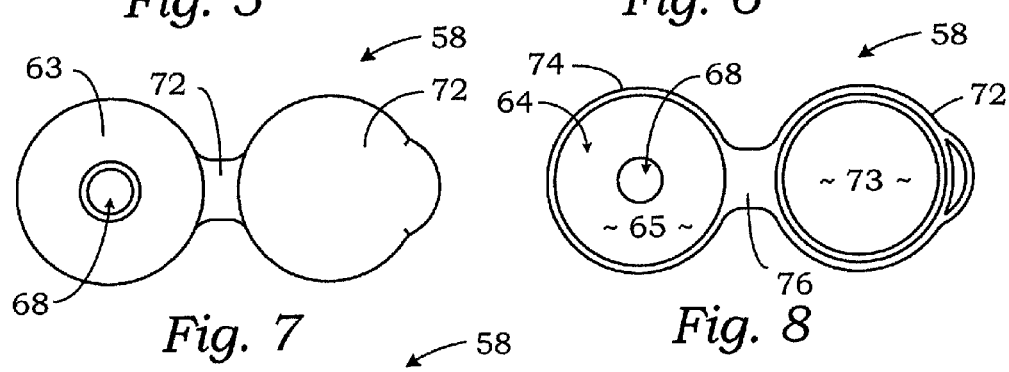
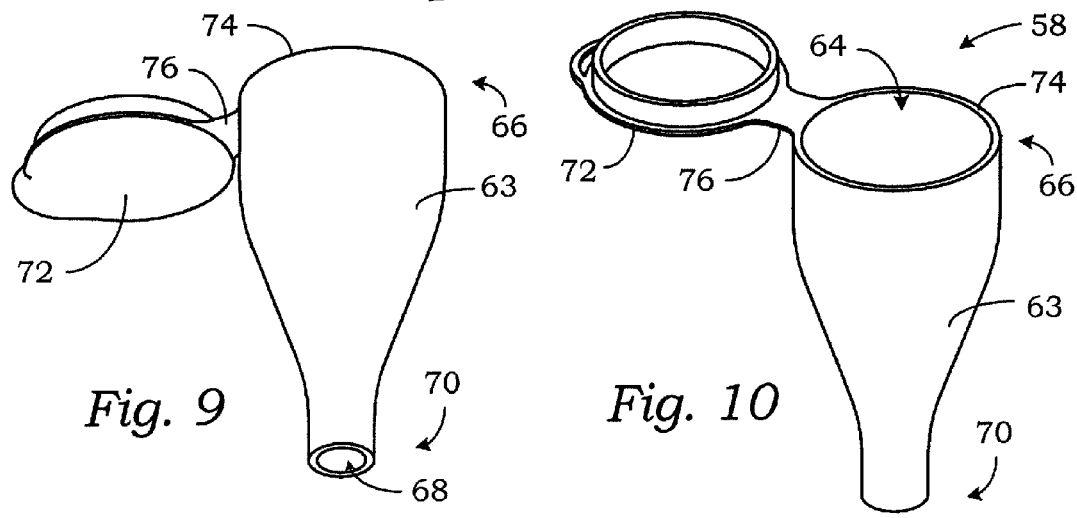

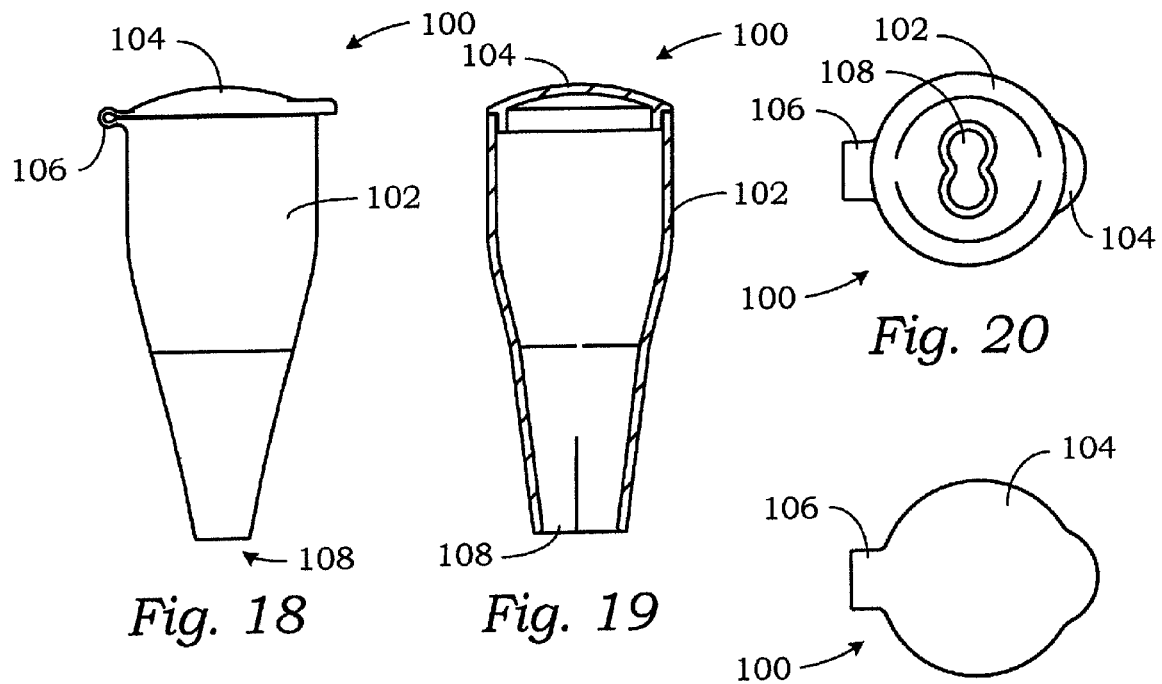
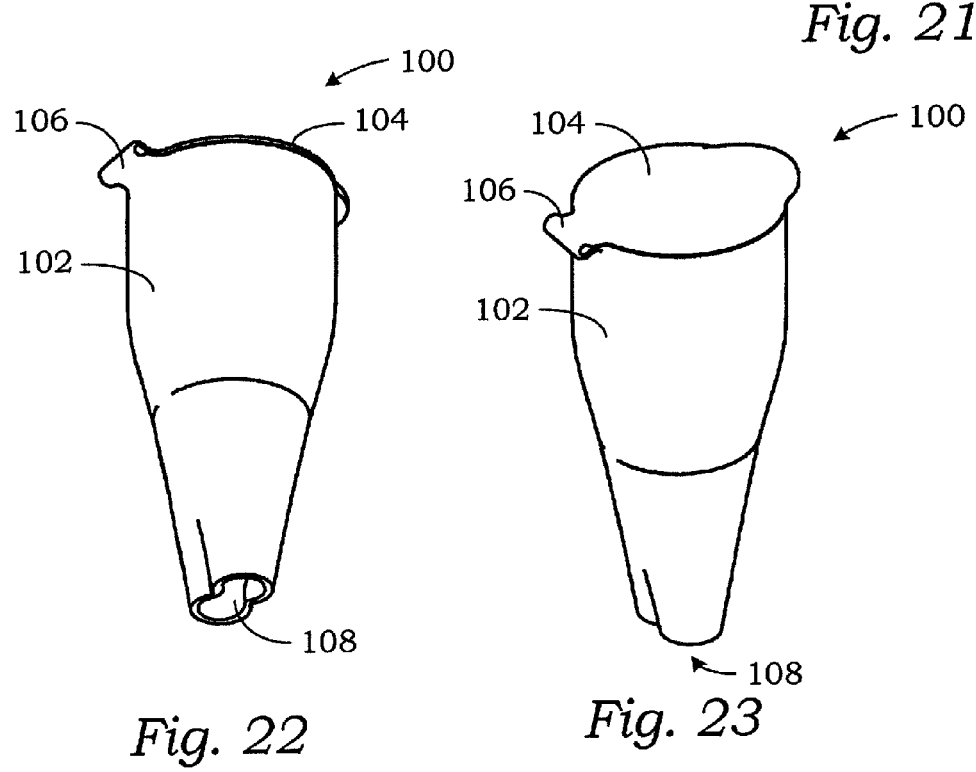
Fig. 18  Fig. 19  Fig. 20
Fig. 21
Fig. 22  Fig. 23

PROTECTIVE STORAGE FOR A NASAL CANNULA ASSEMBLY

FIELD

The present invention relates to nasal oxygen cannulas and, more particularly, to an apparatus for protecting and storing a nasal cannula to reduce contamination.

BACKGROUND

Nasal oxygen cannulas are used to deliver oxygen directly to the nasal airways of a patent to infuse oxygen into the inspirational air flow of the patient. A typical oxygen delivery device utilizing a nasal cannula assembly includes a nasal cannula, a pair of support tubes extending from either end of the cannula, a slide, through which the support tubes pass to tighten the tubing against the patient's neck, a Y-adaptor or manifold connector to divide gas flow between the support tubes, a main supply tubing connected to the Y-adapter or manifold connector and a connector that couples to the oxygen source.

Nasal cannulas are among the most common medical devices in use today, conservatively estimated at several hundred million units annually. Nasal cannulas are widely used in hospitals and surgical centers as well as by patients at home who benefit from long term oxygen therapy. When a cannula is removed from the patient for short periods of time to allow the patient to move about, blow his/her nose, or simply to provide relief from wearing the cannula, it must be hung up or stored somewhere. Often the cannula falls to the floor and becomes contaminated, thus subjecting the patient to an increased risk of respiratory infection when the cannula is reinserted in the patient's nostrils. These patients, especially patients with chronic respiratory diseases, are at an increased susceptibility of developing respiratory infections and suffering severe complications as well as death once doing so. Even a modest reduction in infection rates would correlate to billions of dollars in savings to the healthcare system annually.

SUMMARY

The present invention provides a protective storage apparatus for a nasal oxygen cannula assembly which includes a convenient protective storage capsule to limit environmental exposure when not being used. The nasal cannula may be in a folded or collapsed configuration when in the protective storage capsule. The protective storage capsule may replace the prior art slide and provide the adjustment function of the slide. Alternatively, the protective storage capsule may be slidably positioned on one of the support tubes. The surfaces of the protective storage capsule may be coated with an antimicrobial film or may be infused with antimicrobial particles. When the nasal cannula assembly is removed from the patient, while grasping the protective storage capsule, the supply line may be pulled through the protective storage capsule until the nasal cannula is inside the protective storage capsule shielding the nasal cannula from bacterial contamination and environmental exposure.

BRIEF DESCRIPTION OF THE DRAWINGS

FIG. 5 is an enlarged elevational view of the protective storage capsule of FIG. 2.
FIG. 6 is a side elevational view of the protective storage capsule of FIG. 5.
FIG. 7 is a bottom view of the protective storage capsule of FIG. 5.
FIG. 8 is a top view of the protective storage capsule of FIG. 5.
FIG. 9 is a bottom perspective view of the protective storage capsule of FIG. 5.
FIG. 10 is a top perspective view of the protective storage capsule of FIG. 5.
FIG. 18 is an enlarged front elevational view of alternative embodiment of the protective storage capsule.
FIG. 19 is a side elevational view of the alternative embodiment of the protective storage capsule of FIG. 18.
FIG. 20 is a bottom view of the alternative embodiment of the protective storage capsule of FIG. 18.
FIG. 21 is a top view of the alternative embodiment of the protective storage capsule of FIG. 18.
FIG. 22 is a bottom perspective view of the alternative embodiment of the protective storage capsule of FIG. 18.
FIG. 23 is a top perspective view of the alternative embodiment of the protective storage capsule of FIG. 18.

DETAILED DESCRIPTION

Figure 1:
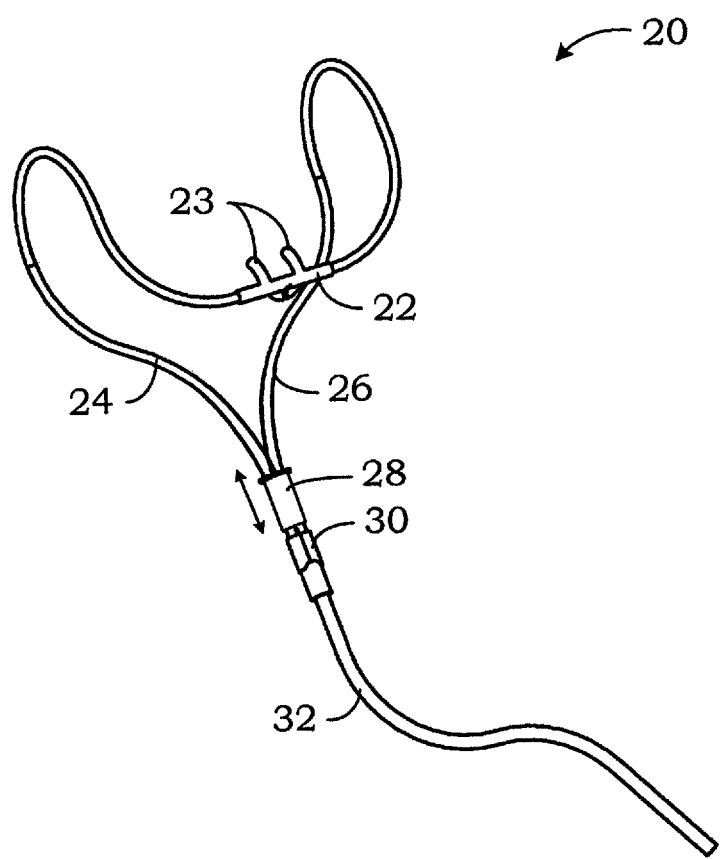
FIG. 1 is a prior art nasal cannula assembly.
Figure 2:
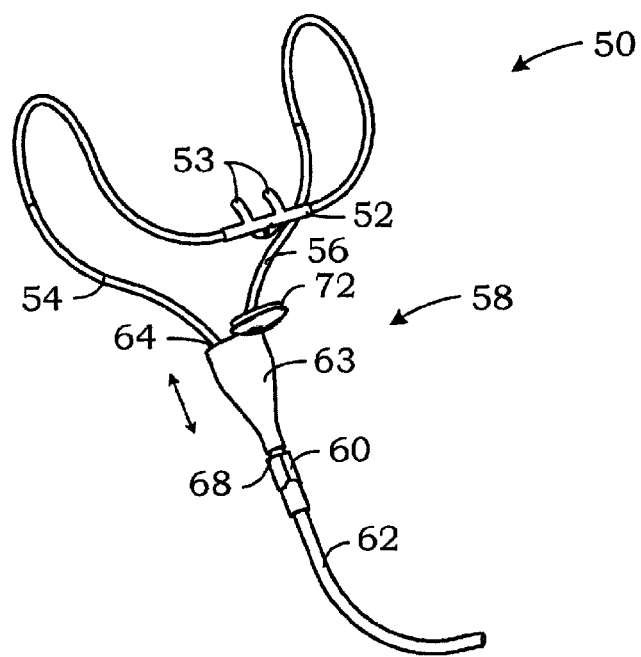
FIG. 2 is a perspective view of a protective storage capsule for a nasal cannula assembly.
Figure 3:
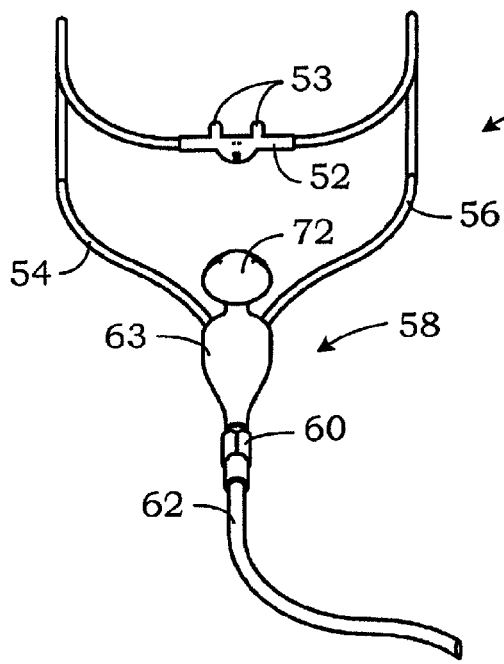
FIG. 3 is a front view of FIG. 2.
Figure 4:
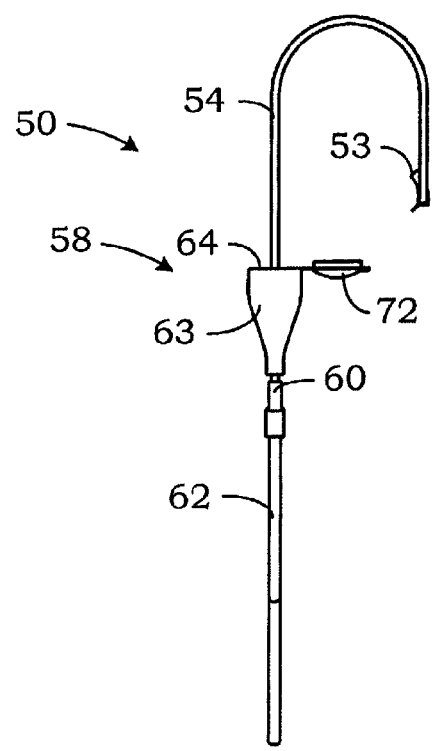
FIG. 4 is a side view of FIG. 2.
Figure 11:
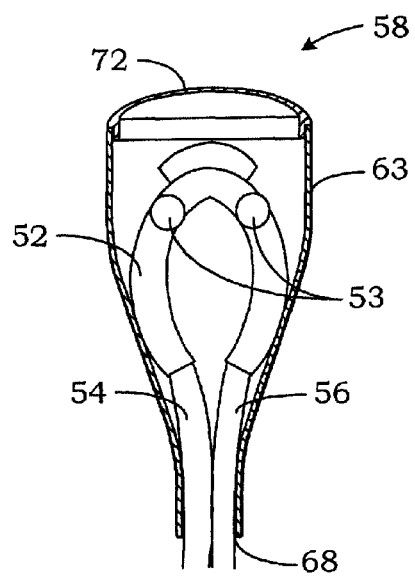
FIG. 11 is a cross-sectional view of the protective storage capsule of FIG. 5 showing the nasal cannula collapsed and stored within the protective storage capsule.
Figure 24:
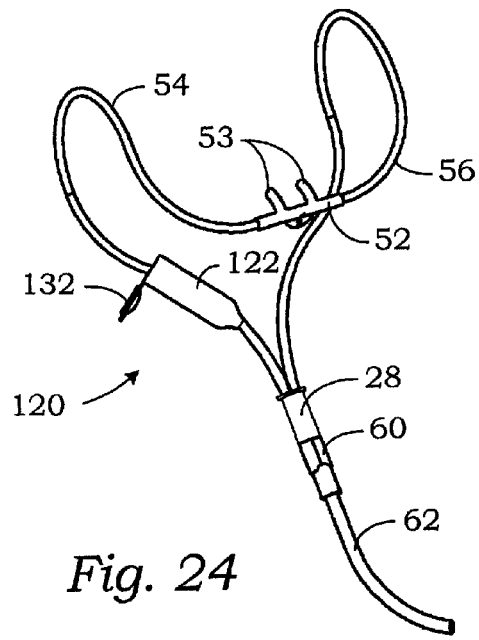
FIG. 24 is a perspective view of an alternative embodiment of a protective storage capsule for a nasal cannula assembly.
Figures 25, 26:
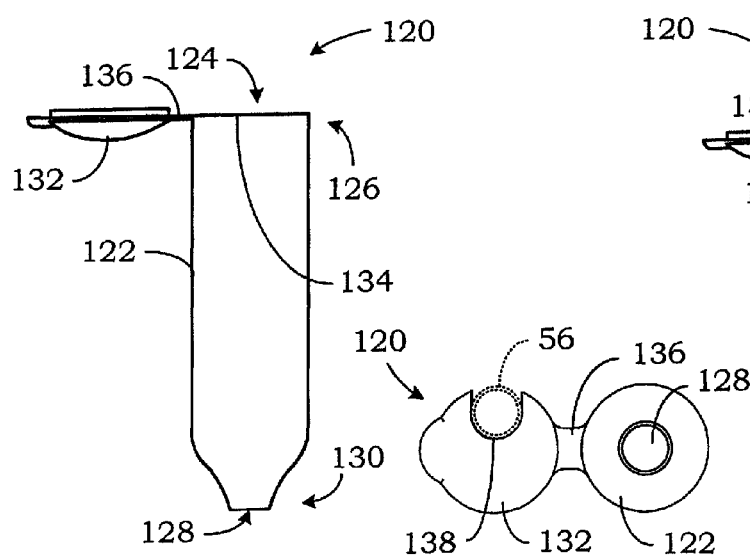
FIG. 25 is an enlarged side elevational view of the alternative embodiment of the protective storage capsule of FIG. 24.
FIG. 26 is a bottom view of the alternative embodiment of the protective storage capsule of FIG. 25.
Figure 27:
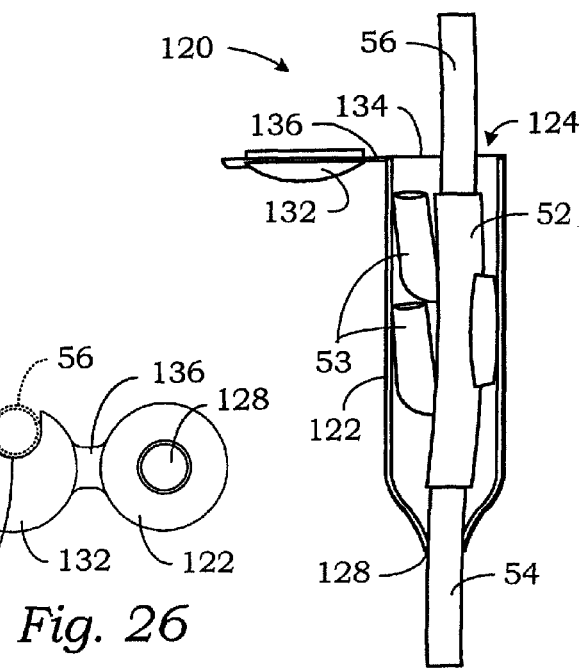
FIG. 27 is a cross-sectional view of the alternative embodiment of the protective storage capsule of FIG. 25 showing the nasal cannula collapsed and stored in the protective storage capsule.
Figure 12:
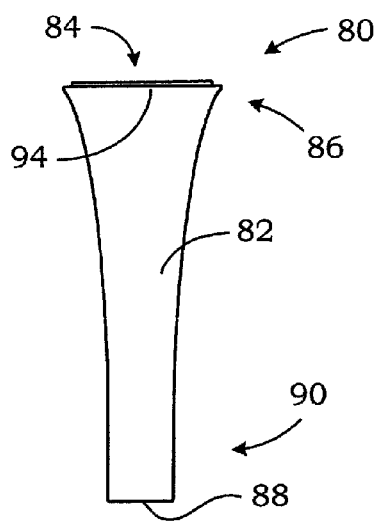
FIG. 12 is an enlarged front elevational view of alternative embodiment of the protective storage capsule.
Figure 13:
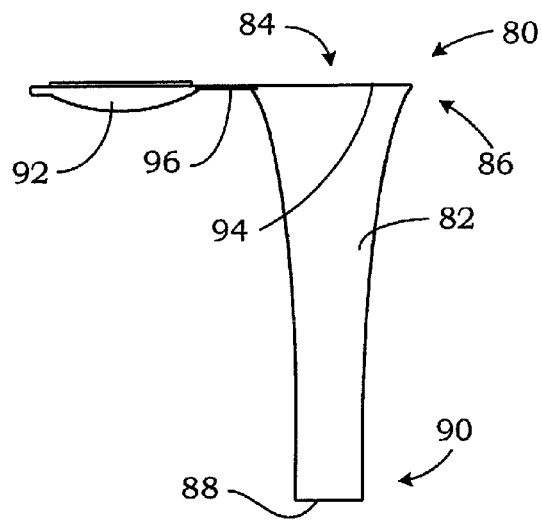
FIG. 13 is a side elevational view of the alternative embodiment of the protective storage capsule of FIG. 12.
Figure 14:
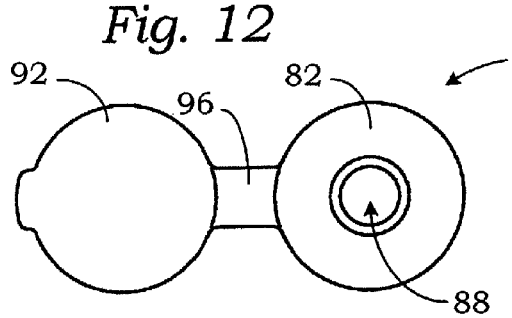
FIG. 14 is a bottom view of the alternative embodiment of the protective storage capsule of FIG. 12.
Figure 15:
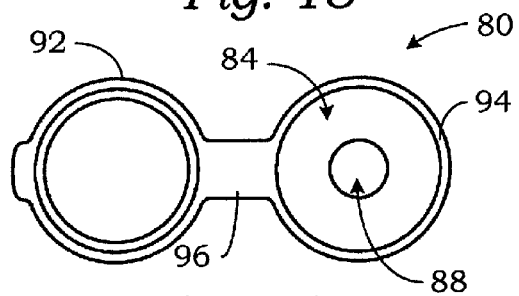
FIG. 15 is a top view of the alternative embodiment of the protective storage capsule of FIG. 12.
Figure 16:
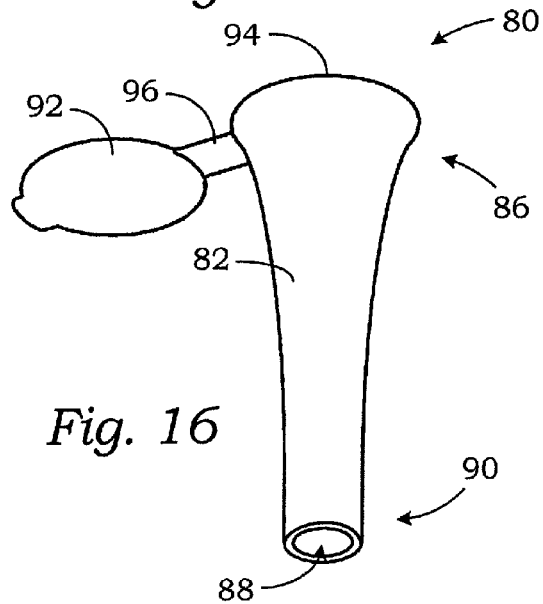
FIG. 16 is a bottom perspective view of the alternative embodiment of the protective storage capsule of FIG. 12.
Figure 17:
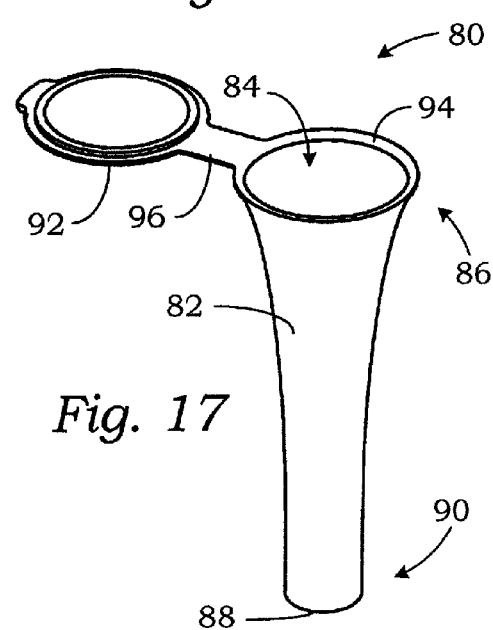
FIG. 17 is a top perspective view of the alternative embodiment of the protective storage capsule of FIG. 12.

Referring initially to FIG. 1, a prior art nasal cannula assembly is generally indicated by reference numeral 20. Nasal cannula assembly 20 includes a nasal cannula 22 including a pair of intra-nasal ports 23, a pair of support tubes 24 and 26 extending from each end of the nasal cannula 20, a slide 28 through which the support tubes 24 and 26 extend, and a Y-adapter or manifold connector 30. The Y-adapter or manifold connector 30 couples the support tubes 24 and 26 to a main supply tube 32 that is coupled to an oxygen source (not shown). The Y-adapter or manifold connector 30 divides the oxygen flow between the support tubes 24 and 26. Slide 28 may be moved up and down along the support tubes 24 and 26 to adjust the fit of the nasal cannula assembly 20 under the chin of a patient.

Referring to FIGS. 2-11, a nasal cannula assembly with a protective storage capsule of the present invention is generally indicated by reference numeral 50. The nasal cannula assembly 50 includes a nasal cannula 52 with a pair of intra-nasal ports 53, a pair of support tubes 54 and 56 extending from each end of the nasal cannula 50, a protective storage capsule 58 and a Y-adapter or manifold connector 60 coupled to a main supply tube 62.

Protective storage capsule 58 includes a generally bell-shaped housing 63 with a large circular opening 64 at one end 66 and a smaller circular opening 68 at the other end 70. Protective storage capsule 58 may be moved up and down along the support tubes 54 and 56 to adjust the nasal cannula assembly 50 under the chin of a patient. A cap 72 is attached to the rim 74 of opening 64 of the bell housing 63 by a flexible hinge 76.

When a patient takes off the nasal cannula assembly 50, the patient may grasp the Y-adapter or manifold connector 60 with one hand and the protective storage capsule 58 with the other hand and pull the two apart. This action pulls the support tubes 54 and 56 through the lower opening 68 of the protective storage capsule 58 until the cannula 52 reaches the large circular opening 64. As the patient continues to pull the support tubes 54 and 56 through the lower opening 68 of the protective storage capsule 58, the cannula 52 bends or folds in half and is pulled into the bell housing 63.

The cannula 52 is typically made of a flexible material such as medical grade polyvinylchloride ("PVC"), high molecular weight PVC, ultra-high molecular weight PVC, PVC/silicone, or other appropriate material, for example, that may be dip molded, injection molded or extruded, for example, into the particular shape desired. The interior surfaces 65 and 73 of the capsule 58 may be treated with an antimicrobial coating. It may be advantageous for all surfaces of the capsule 58 to be treated with a nanocomposite coating of silver and/or gold nanoparticles, or silver sulfadiazine, for example, in a thin surface layer. Alternatively, the interior surfaces 65 and 73, and/or all surfaces of the capsule 58 may be infused with antimicrobial particles such as silver or copper nanoparticles, for example, that protect the surfaces from microbes, and ultimately the patient.

Once the cannula 52 is pulled into the bell housing 63, the cap 72 may be snapped over the opening 64 to seal the cannula 52 inside the protective storage capsule 58. At this point the cannula 52, and in particular the pair of intra-nasal ports 53, are protected from dirt, debris, bacterial contamination and environmental exposure.

When the patient wants to put the nasal cannula assembly 50 back on, he/she opens the cap 72 and pulls the cannula 52 from the bell housing 63. The patient may slide the protective storage capsule 58 down the support tubes 54 and 56 until the lower end 70 encounters the Y-adapter or manifold connector 60. The patient may now put the nasal cannula assembly 50 back on and adjust it as desired.

Referring to FIGS. 12-17, an alternative embodiment of a protective storage capsule for a nasal cannula is generally indicated by reference numeral 80. The protective storage capsule 80 includes a generally trumpet-shaped housing 82 with an opening 84 at one end 86 and a smaller opening 88 at the other end 90. A cap 92 is attached to the rim 94 of opening 84 by a flexible hinge 96. All surfaces of the capsule 80 may be treated with a nanocomposite coating of silver and/or gold nanoparticles, or silver sulfadiazine, for example, in a thin surface layer. Alternatively, the surfaces of the capsule 80 may be infused with antimicrobial particles such as silver or copper nanoparticles, for example, that protect the surfaces from microbes.

Referring to FIGS. 18-23, an alternative embodiment of a protective storage capsule for a nasal cannula is generally indicated by reference numeral 100. The protective storage capsule 100 includes a generally bell-shaped housing 102, a cap 104 shown in a closed position attached to the housing by a flexible hinge 106, and a lower opening 108. Protective storage capsule 100 is generally similar to protective storage capsule 58 with the exception of the lower opening. Lower opening 108 may be generally figure-eight shaped to match the shape of the side-by-side support tubes 54 and 56 to provide a better seal around the support tubes 54 and 56. All surfaces of the capsule 100 may be treated with a nanocomposite coating of silver and/or gold nanoparticles, or silver sulfadiazine, for example, in a thin surface layer. Alternatively, the surfaces of the capsule 100 may be infused with antimicrobial particles such as silver or copper nanoparticles, for example, that protect the surfaces from microbes.

Referring to FIGS. 24-27, an alternative embodiment of a protective storage capsule for a nasal cannula is generally indicated by reference numeral 120. Protective storage capsule 120 includes a cylindrical housing 122 with an opening 124 at one end 126 and a smaller opening 128 at the other end 130. A cap 132 is attached to the rim 134 of opening 124 by a flexible hinge 136. The cap 132 includes a notch or cutout 138 sized to snuggly fit around the support tube 56. The protective storage capsule 120 fits on only one of the support tubes 54 and thus the opening 128 has a diameter matching the outside diameter of the support tube 54. All surfaces of the capsule 120 may be treated with a nanocomposite coating of silver and/or gold nanoparticles, or silver sulfadiazine, for example, in a thin surface layer. Alternatively, the surfaces of the capsule 120 may be infused with antimicrobial particles such as silver or copper nanoparticles, for example, that protect the surfaces from microbes.

To store the nasal cannula 52, the support tube 54 is pulled while grasping the protective storage capsule 120. As the nasal cannula 52 is pulled into the cylindrical housing 122, the intra-nasal ports 53 may fold over in a stored configuration. Once the nasal cannula 52 and intra-nasal ports are completely within the cylindrical housing, the cap 132 is placed over the opening 126 with the notch 134 aligned with the support tube 56 sealing the protective storage capsule 120, and thus protecting the nasal cannula 52, and in particular the intra-nasal ports 53, and ultimately the patient from dirt, debris, bacterial contamination, and environmental exposure. Opening 124 and cylindrical housing 122 may be sized such that the intra-nasal ports 53 need not bend or fold when pulled into the housing 122. Additionally, the housing 122 may have an oval or other geometrical shapes.

To use the nasal cannula 52 again the patient pulls the support tube 56 while grasping the protective storage capsule 120, sliding the protective storage capsule 120 down the other support tube 54, until the nasal cannula 52 is exposed. The flexible intra-nasal ports 53 return to an unfolded normal position. When not storing the nasal cannula 52, the cap 132 of the protective storage capsule 120 may be snapped in place over the opening 124 to seal the protective storage capsule 120 and prevent dirt, debris, and other contaminants from collecting in the protective storage capsule 120.

Figure 28:
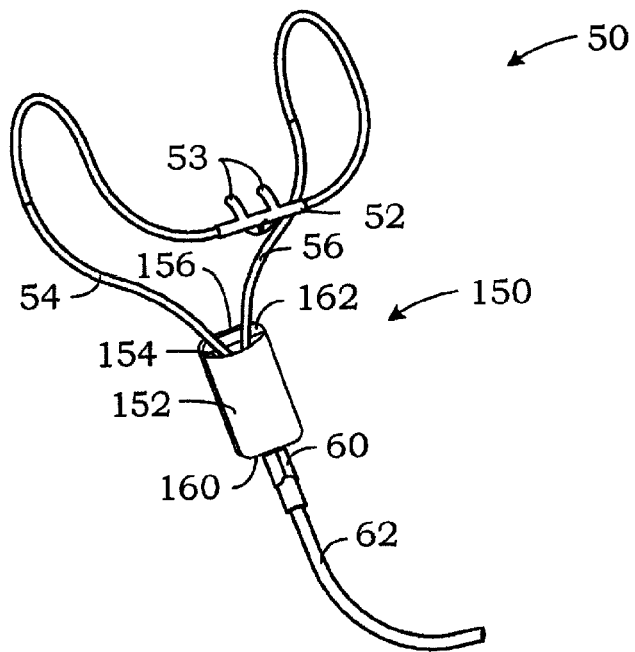
FIG. 28 is a perspective view of an alternative embodiment of protective storage capsule for a nasal cannula assembly.
Figure 29:
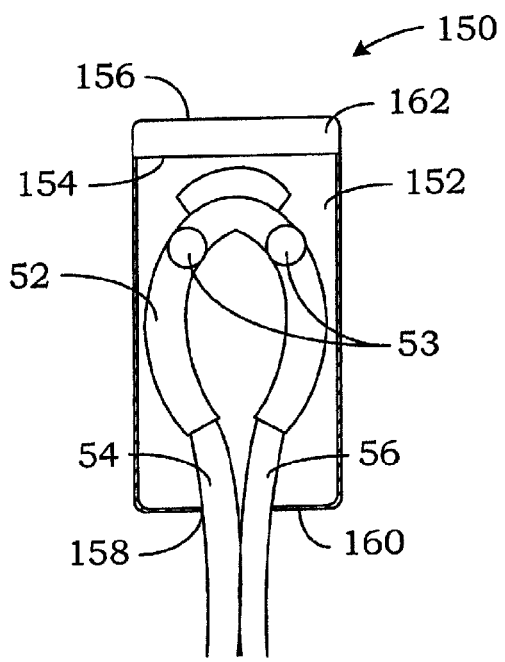
FIG. 29 is an enlarged cross-sectional view of the protective storage capsule of FIG. 28 showing the nasal cannula collapsed and stored in the protective storage capsule.

Referring to FIGS. 28 and 29, an alternative embodiment of a protective storage capsule for a nasal cannula is generally indicated by reference numeral 150. Protective storage capsule 150 includes a rectangular housing 152 with an opening 154 at one end 156 and a lower opening 158 at the other end 160. The rectangular housing 152 may include a flap 162 at the end 156 which may cover the opening 154 when the nasal cannula 52 is stored in the rectangular housing 152. The opening 154 may include a zipper, snap, or Velcro® (not shown), for example, to close the opening 154 when the nasal cannula 52 is stored in the rectangular housing 152. As shown in FIGS. 28 and 29, the protective storage capsule 150 fits on both of the support tubes 54 and 54 and thus the opening 158 may be sized to accommodate the outside diameter of the support tube 54 and 56. Alternatively, the protective storage capsule 150 may be sized to fit on one support tube 54 similar to the embodiment shown in FIGS. 24-27. All surfaces of the capsule 150 may be treated with a nanocomposite coating of silver and/or gold nanoparticles, or silver sulfadiazine, for example, in a thin surface layer. Alternatively, the surfaces of the capsule 150 may be infused with antimicrobial particles such as silver or copper nanoparticles, for example, to protect the surfaces from microbes.

When a patient takes the nasal cannula assembly 50 off, the patient may grasp the Y-adapter or manifold connector 60 with one hand and the protective storage capsule 150 with the other hand and pull the two apart. The action pulls the support tubes 54 and 56 through the lower opening 158 of the protective storage capsule 150 until the cannula 52 reaches the opening 154. As the patient continues to pull the support tubes 54 and 56 through the lower opening 158 of the protective storage capsule 150, the cannula 52 bends or folds in half and is pulled into the rectangular housing 152. Once the cannula 52 is pulled into the rectangular housing 152, the flap 162 cover the opening 154 to protect the cannula 52 in the protective storage capsule 150. Alternatively, a zipper, snap, Velcro® or other closure (not shown) may be employed to seal the opening 154 and protect the cannula 52. At this point the cannula 52, and in particular the pair of intra-nasal ports 53, are protected from dirt, debris, bacterial contamination and environmental exposure.

When the patient wants to put the nasal cannula assembly 50 back on, he/she opens the flap 162 and pulls the cannula 52 from the rectangular housing 152. The patient may slide the protective storage capsule 150 down the support tubes 54 and 56 until the lower end 160 encounters the Y-adapter or manifold connector 60. The patient may now put the nasal cannula assembly 50 back on and adjust it as desired.

It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is:

1. A protective storage capsule for a nasal cannula of a nasal cannula assembly worn by a patient, the nasal cannula assembly including the nasal cannula, a pair of support tubes extending from opposite ends of the nasal cannula, a manifold connector joining the pair of support tubes to a main supply tube, said protective storage capsule comprising:
   a housing having a first opening adapted to receive the nasal cannula, a second opening adapted to slidably receive the pair of support tubes therethrough, said first opening larger than said second opening, said second opening sized to prohibit passage of the nasal cannula therethrough, said housing narrowing from said first opening to said second opening,
   a cap adapted to fit over said first opening in said housing, said cap secured to said housing using a flexible hinge,
   wherein said housing may be slid in a first direction along the support tubes to tighten the nasal cannula assembly worn by the patient,
   wherein said housing may be slid in a second direction along the support tubes to loosen the nasal cannula assembly,
   wherein the nasal cannula may be pulled into said housing by sliding said housing in said first direction until the nasal cannula is in a stored position within said housing, and
   wherein said cap may be secured over said first opening when the nasal cannula is in said stored position.

2. The protective storage capsule of claim 1 wherein said housing is generally bell shaped.

3. The protective storage capsule of claim 1 wherein said housing is generally trumpet shaped.

4. The protective storage capsule of claim 1 wherein said housing is generally conically shaped.

5. The protective storage capsule of claim 1 wherein said second opening has a generally circular shape.

6. The protective storage capsule of claim 1 wherein said second opening has a generally figure-eight shape.

7. The protective storage capsule of claim 1 wherein said housing includes an interior surface and said cap includes an interior surface, and wherein said interior surface of said housing and said interior surface of said cap are treated with an antimicrobial film.

8. The protective storage capsule of claim 1 wherein said housing includes an interior surface and said cap includes an interior surface, and wherein said interior surface of said housing and said interior surface of said cap are infused with antimicrobial particles.

9. The protective storage capsule of claim 1 wherein said housing is treated with an antimicrobial film.

10. The protective storage capsule of claim 1 wherein said cap is treated with an antimicrobial film.

11. The protective storage capsule of claim 1 wherein said housing is treated with antimicrobial particles.

12. The protective storage capsule of claim 1 wherein said cap is treated with antimicrobial particles.

13. A protective storage capsule for a nasal cannula of a nasal cannula assembly worn by a patient, the nasal cannula assembly including the nasal cannula, a pair of support tubes extending from opposite ends of the nasal cannula, a manifold connector joining the pair of support tubes to a main supply tube, said protective storage capsule comprising:
   a housing having a first opening adapted to receive the nasal cannula, a second opening adapted to slidably receive at least one support tube from the pair of support tubes therethrough, said first opening larger than said second opening, said second opening sized to prohibit passage of the nasal cannula therethrough, said housing narrowing from said first opening to said second opening,
   a cap adapted to fit over said first opening in said housing, said cap secured to said housing using a flexible hinge,
   wherein said housing may be slid in a first direction along at least one of the support tubes to tighten the nasal cannula assembly worn by the patient,
   wherein said housing may be slid in a second direction along at least one of the support tubes to loosen the nasal cannula assembly,
   wherein the nasal cannula may be pulled into said housing by sliding said housing in said first direction until the nasal cannula is in a stored position within said housing, and wherein said cap may be secured over said first opening of said housing when the nasal cannula is in said stored position.

14. The protective storage capsule of claim 13 wherein said housing is generally bell shaped.

15. The protective storage capsule of claim 13 wherein said housing is generally trumpet shaped.

16. The protective storage capsule of claim 13 wherein said housing is generally conically shaped.

17. The protective storage capsule of claim 13 wherein said second opening has a generally circular shape.

18. The protective storage capsule of claim 13 wherein said second opening has a generally figure-eight shape.

19. The protective storage capsule of claim 13 wherein said cap includes a notch adapted to receive at least one support tube from the pair of support tubes when said cap is secured over said first opening of said housing.

20. The protective storage capsule of claim 13 wherein said housing includes an interior surface and said cap includes an interior surface, and wherein said interior surface of said housing and said interior surface of said cap are treated with an antimicrobial film.

21. The protective storage capsule of claim 13 wherein said housing includes an interior surface and said cap includes an interior surface, and wherein said interior surface of said housing and said interior surface of said cap are infused with antimicrobial particles.

22. The protective storage capsule of claim 13 wherein said housing is treated with an antimicrobial film.

23. The protective storage capsule of claim 13 wherein said cap is treated with an antimicrobial film.

24. The protective storage capsule of claim 13 wherein said housing is treated with antimicrobial particles.

25. The protective storage capsule of claim 13 wherein said cap is treated with antimicrobial particles.

26. A protective storage capsule for a nasal cannula of a nasal cannula assembly worn by a patient, the nasal cannula assembly including the nasal cannula, a pair of support tubes extending from opposite ends of the nasal cannula, a manifold connector joining the pair of support tubes to a main supply tube, said protective storage capsule comprising:

a housing having a first opening adapted to receive the nasal cannula, a second opening adapted to slidably receive at least one support tube from the pair of support tubes therethrough, said first opening larger than said second opening, said second opening sized to prohibit passage of the nasal cannula therethrough, said housing narrowing from said first opening to said second opening, and wherein the nasal cannula may be pulled into said housing by sliding said housing in a first direction until the nasal cannula is in a stored position within said housing.

27. The protective storage capsule of claim 26 wherein said housing is generally bell shaped.

28. The protective storage capsule of claim 26 wherein said housing is generally trumpet shaped.

29. The protective storage capsule of claim 26 wherein said housing is generally conically shaped.

30. The protective storage capsule of claim 26 wherein said housing is generally pouch shaped.

31. The protective storage capsule of claim 26 wherein said second opening has a generally circular shape.

32. The protective storage capsule of claim 26 wherein said second opening has a generally figure-eight shape.

33. The protective storage capsule of claim 26 wherein said housing includes an interior surface, and wherein said interior surface of said housing is treated with an antimicrobial film.

34. The protective storage capsule of claim 26 wherein said housing includes an interior surface, and wherein said interior surface of said housing is infused with antimicrobial particles.

35. The protective storage capsule of claim 26 wherein said housing is treated with an antimicrobial film.

36. The protective storage capsule of claim 26 wherein said housing is treated with antimicrobial particles.

37. The protective storage capsule of claim 26 further comprising a cap adapted to fit over said first opening in said housing, wherein said cap may be secured over said first opening of said housing when the nasal cannula is in said stored position.

38. The protective storage capsule of claim 37 wherein said cap includes a notch adapted to receive at least one support tube from the pair of support tubes when said cap is secured over said first opening of said housing.

39. The protective storage capsule of claim 37 wherein said cap is treated with an antimicrobial film.

40. The protective storage capsule of claim 37 wherein said cap is treated with antimicrobial particles.

\* \* \* \* \*